United States Patent
Tanihara et al.

[11] Patent Number: 5,880,216
[45] Date of Patent: Mar. 9, 1999

[54] POLYVINYL ALCOHOL AND GEL CONTAINING THE SAME

[75] Inventors: Masao Tanihara; Yoshiharu Fukunishi, both of Kurashiki, Japan

[73] Assignee: Kuraray Co., Ltd., Kurashiki, Japan

[21] Appl. No.: 772,463

[22] Filed: Dec. 23, 1996

[30] Foreign Application Priority Data

Dec. 22, 1995 [JP] Japan ..................................... 7-350488
Jun. 26, 1996 [JP] Japan ..................................... 8-185466

[51] Int. Cl.$^6$ ..................................................... C08G 63/91
[52] U.S. Cl. .............................. 525/61; 525/59; 526/277; 526/287
[58] Field of Search .................................. 525/59, 60, 61; 526/277, 287, 318.1, 318.2

[56] References Cited

U.S. PATENT DOCUMENTS

| | | |
|---|---|---|
| 2,495,108 | 1/1950 | Kosolapoff . |
| 4,707,516 | 11/1987 | Janouch ...................................... 525/61 |
| 5,187,226 | 2/1993 | Kamachi et al. ........................... 525/56 |
| 5,278,022 | 1/1994 | Wade .......................................... 525/61 |

FOREIGN PATENT DOCUMENTS

| | | |
|---|---|---|
| 0 249 306 | 12/1987 | European Pat. Off. . |
| 0 389 833 | 10/1990 | European Pat. Off. . |
| 0 583 170 | 2/1994 | European Pat. Off. . |
| 2 109 103 | 5/1972 | France . |
| 58-92359 | 6/1983 | Japan . |
| 3-215417 | 9/1991 | Japan . |
| 1165486 | 10/1969 | United Kingdom . |
| WO 90/01954 | 3/1990 | WIPO . |
| WO 92/03172 | 3/1992 | WIPO . |

OTHER PUBLICATIONS

Journal of Biomedical Materials Research, vol. 28, pp. 1165–1173, 1994, D. Chakravarthy, et al., "Evaluation of Three New Hydrocolloid Dressings: Retention of Dressing Integrity and Biodegradability of Absorbent Components Attenuate Inflammation".

Emerg. Med. Clin. North. Amer., vol. 10, No. 4, pp. 655–663, Nov. 1992, John M. Howell, "Current and Future Trends in Wound Healing".

J. Am.Acad.Dermatol., vol. 12, pp. 434–440, 1985, William H. Eaglstein, "Experiences with Biosynthetic Dressings", No. 2, Part 2.

J. Invest. Dermatol., vol. 97, No. 3, pp. 586–592, Sep. 1991, Stephen R. Young, et al., Comparison of The Effects of Semi–Occlusive Polyurethane Dressings And Hydrocolloid Dressings On Dermal Repair: 1. Cellular Changes.

*Primary Examiner*—Paul R. Michl
*Attorney, Agent, or Firm*—Oblon, Spivak, McClelland, Maier & Neustadt, P.C.

[57] ABSTRACT

A polyvinyl alcohol is provided containing structural units of the following formula (I) at a molar fraction of 0.05–0.50 and the structural units of the following formula (II) at a molar fraction of 0.0001 to 0.50;

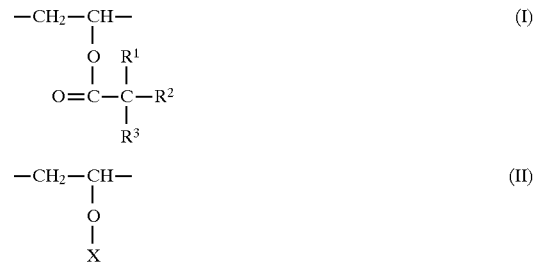

wherein $R^1$, $R^2$, $R^3$ and X are as desribed herein, and its use in preparation of gels, particularly hydrogels, effective for use in wound dressing materials.

2 Claims, No Drawings

POLYVINYL ALCOHOL AND GEL CONTAINING THE SAME

BACKGROUND OF THE INVENTION

1. Field of the Invention

The present invention relates to a new polyvinyl alcohol, a gel base material and a gel, both containing the polyvinyl alcohol, and a wound dressing material primarily comprising the gel.

2. Description of the Prior Art

Gels, particularly polymer hydrogels containing water as the medium, have been conventionally used in practice in a wide variety of fields. In the food field in particular, use has been made of a variety of gel base materials comprising natural polymers, such as agar, gelatin, konjakmannan and the like; and foodstuffs of hydrogels comprising these gel base materials have been commonly used.

Recently, the development of application techniques of versatile gel functions has made progress in a wider field, and, accordingly, the field of gel application has been enlarged steadily. For example, the development of highly biocompatible gels has been remarkable, including the development of highly water-absorbable gels used in products such as disposable diapers and hygienic napkins, gels to immobilize enzymes and bacteria, contact lenses, artificial muscles, artificial organs, and wound dressings.

Following the progress of gel basic science, represented by the discovery of the phase transition phenomenon of gels, diverse attempts have been made to apply gels to highly functional products such as sensors, functional separation membranes, release control membranes, switches, and actuators.

Polymer compounds as gel base materials can be divided into natural polymers, represented by gelatin and a variety of polysaccharides, and synthetic polymers such as polyacrylic acid, poly(2-hydroxyethyl methacrylate), polyacrylamide, and polyvinyl alcohol. However, recent innovative gel applications have demanded base materials with flexibility, transparency, resistance to moist heat and resistance to hot water, making the development of a polymer base material capable of forming such a gel desirable.

As noted above, one important gel application is in wound dressing materials. It is generally required that wound dressing materials should occlusively hold a variety of healing-promoting growth factors contained in the wound exudate onto the wound to promote healing. Gauze and ointments conventionally used for treating wounds, such as lacerations, burns, ulcers and bed sores, operate by absorbing the exudate from the wound site and preventing the extraneous infiltration of bacteria and the like. It has been recently determined that a variety of growth factors (for example, bFGF, TGF β, etc.) that promote healing are present in the exudate from wounds [see Howell, J. M., Current and Future Trends in Wound Healing, Emerg. Med. Clin. Amer., 10, 655–663 (1992), etc.]. Thus, attention has been focused on occlusive dressing materials exerting an effect of promoting wound healing by holding these growth factors on the wounds [see Eaglestein, W. E., Experience with biosynthetic dressings, J. Am. Acad. Dermatol., 12, 434–440 (1985)].

Such occlusive wound dressing materials include conventional materials such as polyurethane films, hydrocolloids, and non-woven fabrics comprising alginate fiber, and polyvinyl alcohol sponge, as well as hydrogels such as polyvinyl alcohol hydrogel, polyethylene glycol hydrogel, and polyacrylamide hydrogel. More specifically, various publications have proposed the following occlusive wound dressing materials;

1. a wound treating device made of a non-woven fiber fabric of a mixture of an insoluble alginate and a soluble alginate (WO 90/01954);

2. a wound dressing material produced by incorporating a hydrogel of a borate-modified gum guaiac in the pores of an open-cell foam comprising a biocompatible synthetic material, and then attaching a peptide that promotes wound healing, through a free hydroxyl group and/or an amino group and a bifunctional coupling agent, on the surface of the hydrogel, and/or making the hydrogel contain an antiseptic or anti-fungal substance (WO 92/03172);

3. a wound dressing material comprising a hydrogel formed from a polyvinyl alcohol with a saponification degree of 95 mol % or more and a viscosity average polymerization degree of 1500 or more and a water-soluble organic compound having two to eight hydroxyl groups (Japanese Patent Application Kokai (Laid-open) No. Sho 58-92359);

4. a semi-transparent, water-insoluble hydrogel in semi-crystals for use as a wound dressing material, which is produced by physically cross-linking polyvinyl alcohol and a complexing agent such as poly(methyl vinyl ether/maleic anhydride) (EP 0583170); and 5. a long active substance for use as a wound dressing material, produced by incorporating pilocarpine hydrochloride and the like in a polyvinyl alcohol hydrogel including hyaluronic acid and/or the salt thereof [Japanese Patent Application Kokai (Laid-open) No. Hei 3-215417].

Among the above-noted conventionally known wound dressing materials, wound dressing materials comprising a polyurethane film are satisfactory to some extent with respect to transparency and occlusiveness. However, due to their inability to absorb water, the polyurethane wound dressing materials cannot be applied to wounds having a lot of exudate.

Some polyethylene glycol hydrogels and polyacrylamide hydrogels are transparent. However, such gels can induce chronic inflammation due to contact with the wound. Further, the raw material monomers of these two types of gels are so highly toxic that the monomers remaining in the hydrogels or the degradation products of these gels may potentially exert their toxicity.

Although wound treating devices comprising hydrocolloids, polyvinyl alcohol sponges and non-woven fabrics of a alginate fiber mixture have the ability to retain exudate, the devices are unfortunately so opaque that wounds cannot be observed through them. Furthermore, it has been reported that the principal components of hydrocolloid wound dressing materials that remain in repaired tissues for a prolonged period can trigger chronic inflammation [see Young, S. R. et al., Comparison of the Effect of Semi-occlusive Polyurethane Dressings and Hydrocolloid Dressings on Dermal Repair: 1. Cellular Changes, J. Invest. Dermatol., 97, 586–592 (1991)].

Once bacterial infection occurs during the attachment of these wound dressing materials, the moist environment serves as such a suitable medium for bacteria that the bacteria grow rapidly to possibly develop into a severe infection.

Furthermore, in the above-noted item 2, a wound healing-promoting peptide is chemically bonded onto the surface of the wound dressing material and the chemical bonding is never broken. Therefore, the effect can be exerted only at the site in contact with the wound dressing material.

Furthermore, while the wound dressing material described above in item 3 has some degree of mechanical strength, if the material is attached onto a wound site, the site cannot be observed through the material because of its opaqueness. Additionally, the material is solubilized during a conventional steam sterilization process at a temperature of 121° C. for 20 minutes. Thus, the material has such poor resistance to moist heat that it cannot be completely sterilized. Additionally, the wound dressing material is not safe since it contains high levels of solubilized matter even at a temperature at which the material itself is not solubilized.

The hydrogel described above in item 4 is semitransparent at a thickness of 1000 µm or less, but the hydrogel does not have sufficient transparency that wounds can be observed through the hydrogel even at this thickness. In order to provide satisfactory water absorptivity as an occlusive wound dressing material, the hydrogel should be of a thickness above 1,000 µm. In that case, however, the hydrogel turns opaque or nearly opaque, so that observation of wounds is much more difficult. Furthermore, because the completing agent is bonded to the polyvinyl alcohol by a physical cross-linking in the hydrogel, the hydrogel cannot be steam sterilized. Thus, the hydrogel cannot be sterilized completely. Additionally, the hydrogel contains high levels of solubilized matter even at low temperatures at which the hydrogel itself cannot be solubilized, and therefore, the hydrogel is of insufficient safety. Thus, the hydrogel is not suitable as a wound dressing material.

The polyvinyl alcohol hydrogel described above in item 5 may be prepared as a transparent material, depending on the production process, but the gel has poor handleability due to low physical strength. The gel, having a low cross-linking degree, cannot be steam sterilized so the gel cannot be sterilized completely. Furthermore, the hydrogel also contains high levels of solubilized matter even at a temperature at which the gel itself is not solubilized, so the gel is less safe. Additionally, when the degree of cross-linking of the hydrogel is elevated under irradiation, problems may occur, such as breaking of the main chain via radiation, decrease of the water content, decrease in flexibility and the like. Thus, the gel does not have sufficient physical properties for use as a wound dressing material.

SUMMARY OF THE INVENTION

Accordingly, one object of the present invention is to provide a polyvinyl alcohol capable of forming a gel having high transparency and flexibility, excellent resistance to moist heat and good resistance to hot water.

A further object of the present invention is to provide a polyvinyl alcohol that can be converted to a gel that is able to be steam sterilized and withstand boiling in water.

A further object of the present invention is to provide a polyvinyl alcohol that can provide a gel having superior water absorptivity and occlusiveness, and involving less solubilized matter at greater safety, whereby the gel can form a hydrogel or a solvent-containing gel capable of being effectively applied to a variety of end uses, such as wound dressing materials, the base material for patches, gels for immobilizing enzymes or bacteria, contact lenses, artificial muscles, artificial cartilage, artificial joints, artificial organs, sensors, functional separation membranes, release control membranes, switches, actuators, and micro-machines.

Another object of the present invention is to provide a gel base material and a gel, primarily comprising the polyvinyl alcohol.

A further object of the present invention is to provide a wound dressing material primarily comprising the gel.

These and other objects of the present invention have been satisfied by the discovery of a polyvinyl alcohol comprising (i) one or more structural units represented by the following formula (I):

wherein the structural units of formula (I) are present at a molar fraction of 0.05 to 0.50; and (ii) at least one structural unit represented by the following formula (II):

wherein the structural units of formula (II) are present at a molar fraction of 0.0001 to 0.50, and its use in preparing a gel.

DETAILED DESCRIPTION OF THE PREFERRED EMBODIMENTS

The present invention relates to a polyvinyl alcohol comprising a 0.05 to 0.50 molar faction of a structural unit represented by the following formula (I)

wherein $R^1$ is hydrogen atom or a monovalent hydrocarbon group; and $R^2$ and $R^3$ are, independently, a monovalent hydrocarbon group or $R^2$ and $R^3$ together form a ring along with the carbon atom to which $R^2$ and $R^3$ are bonded; or $R^1$, $R^2$ and $R^3$ together form a ring along with the carbon atom to which $R^1$, $R^2$ and $R^3$ are bonded (referred to as "structural unit (I)" hereinafter) and a 0.0001 to 0.50 molar fraction of a structural unit represented by the following formula (II)

wherein X is a group represented by the formula —CO—Y, -Y or —COCOOH, wherein Y represents a hydrocarbon group modified with at least one polar group selected from the group consisting of carboxyl, sulfo, amino and phosphonooxy; or Y represents a hydrocarbon group modified with a group having at least one polar group selected from the group consisting of carboxyl, sulfo, amino and phosphonooxy; or X forms a phosphonooxy group together with the oxygen atom to which X is bonded (referred to as "structural unit (II)" hereinbelow).

The present invention preferably includes a polyvinyl alcohol wherein the molar fraction of the structural unit (II) satisfies the following formula (1);

$$\{(1-C_{est}) \times C_{est}\} \times 0.01 \leq C_{pol} < \{(1-C_{est}) \times C_{est}\} \times 2.0 \quad (1)$$

wherein $C_{pol}$ is the molar fraction of the structural unit represented by formula (II); and $C_{est}$ is the molar fraction of the structural unit represented by formula (I) and a polyvinyl alcohol wherein the average chain length ($L_{est}$) of the structural unit (I), represented by the following formula (2) is 2.0 or more;

$$L_{est} = (C_{est}/C_{met}) \times 2 \quad (2)$$

wherein $L_{est}$ is the average chain length of the structural unit (I); $C_{est}$ is the molar fraction of the structural unit (I); and $C_{met}$ is the molar fraction of the methylene carbon interposed between the methine carbon bonded with the hydroxyl group or a group represented by the formula —OX and the methine carbon composing the structural unit (I), among the methylene carbons composing the main chain of the polyvinyl alcohol.

The present invention includes a gel base material containing the polyvinyl alcohol described above, and a gel produced from the gel base material.

Furthermore, the present invention is a wound dressing material primarily comprising the gel described above.

The polyvinyl alcohol of the present invention is a polyvinyl alcohol, containing structural units represented by the formula (I) and structural units represented by the formula (II), as the essential structural units.

The term "gel base material" in accordance with the present invention refers to the polyvinyl alcohol base material to be used for forming gel (namely, the polyvinyl alcohol before gelation).

The term "gel" in accordance with the present invention means a gel containing water and/or an organic solvent and comprising the polyvinyl alcohol in a gel form.

In the structural unit (I) contained in the polyvinyl alcohol of the present invention, the group $R^1$ is hydrogen atom or a mono-valent hydrocarbon group; and $R^2$ and $R^3$ are, each independently, a mono-valent hydrocarbon group or $R^2$ and $R^3$ together form a ring along with the carbon atom to which $R^2$ and $R^3$ are bonded; or $R^1$, $R^2$ and $R^3$ together form a ring along with the carbon atom to which $R^1$, $R^2$ and $R^3$ are bonded.

In the structural unit (I), $R^2$ and $R^3$ may be the same mono-valent hydrocarbon group or may be different mono-valent hydrocarbon groups, individually, when $R^1$ is hydrogen atom.

When all of $R^1$, $R^2$ and $R^3$ are mono-valent hydrocarbon groups, all of the three may be the same mono-valent hydrocarbon group; or two of them may be the same mono-valent hydrocarbon group while the remaining one is a different hydrocarbon group or the three groups may be different mono-valent hydrocarbon groups.

When $R^1$, $R^2$ and $R^3$ are mono-valent hydrocarbon groups in the structural unit (I), the hydrocarbon groups are preferably a linear or branched alkyl group having from 1 to 18 carbon atoms, preferably from 1 to 8 carbons, a mono-valent aromatic hydrocarbon group having from 6 to 18 carbon atoms, preferably from 6 to 10 carbons, or a cycloalkyl group having from 3 to 12 carbons, preferably from 5 to 8 carbons, with no limitation. Suitable groups for $R^1$, $R^2$ or $R^3$ include alkyl groups, such as methyl, ethyl, propyl, n-butyl, t-butyl, hexyl, pentyl, octyl, lauryl, and stearyl; monovalent aromatic groups, such as phenyl, naphthyl, and anthryl; cycloalkyl groups, such as cyclohexyl, bicyclo[3.1.0]hexyl, and bicyclo[2.2.0]hexyl.

When $R^2$ and $R^3$ together form a ring along with the carbon atom to which $R^2$ and $R^3$ are bonded or when $R^1$, $R^2$ and $R^3$ together form a ring along with the carbon atom to which $R^1$, $R^2$ and $R^3$ are bonded, the ring is preferably a saturated hydrocarbon ring or unsaturated hydrocarbon ring; more preferably a benzene ring, a cyclohexane ring, a norbornane ring, an adamantane ring, a noradamantane ring, or a naphthalene ring.

The structural unit (I) is specifically exemplified, with no limitation, as a structural unit represented by the following chemical formulae;

(Ia)

(Ib)

(Ic)

(Id)

(Ie)

(If)

(Ig)

(Ih)

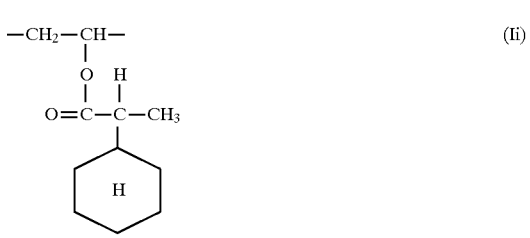
(Ii)

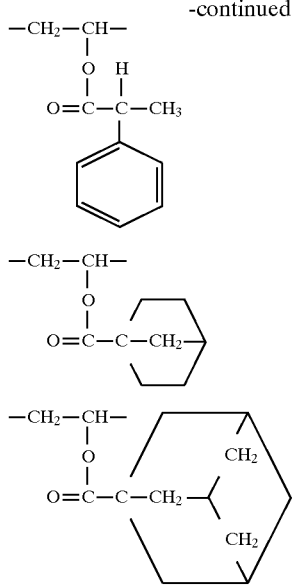

The polyvinyl alcohol in accordance with the present invention can contain one or more different structural units of formula (I) in the main chain.

In accordance with the present invention, preferably, the structural unit (I) of the polyvinyl alcohol is either one of the structural units (Ia) and (Ib) or both thereof, from the respect of gel mechanical strength and ready production of the polyvinyl alcohol.

In the structural unit (II), contained in the main chain of the polyvinyl alcohol together with the structural unit (I), X is a group represented by the formula —CO—Y, -Y or —CO—COOH or X forms a phosphonooxy group together with the oxygen atom to which X is bonded.

In the structural unit (II) wherein X is a group represented by the formula —CO—Y or the formula -Y, the group Y may be either:

(i) a hydrocarbon group modified with at least one polar group selected from carboxyl, sulfo, amino and phosphonooxy groups, preferably where the polar group is directly bonded to the carbon atom of the hydrocarbon group that is bonded to the oxygen atom of the hydroxyl group of the polyvinyl alcohol; or (ii) a hydrocarbon group modified with a substituent having at least one polar group selected from carboxyl, sulfo, amino and phosphonooxy groups, preferably wherein the at least one polar group is not directly bonded to the carbon atom of the hydrocarbon group that is bonded to the oxygen atom of the hydroxyl group of the polyvinyl alcohol. Rather the polar group is bonded to a different group or bonded to the hydrocarbon group via a different bond.

In either of the above cases (i) and (ii), the group Y is a hydrocarbon group having at least one polar group selected from carboxyl, sulfo, amino, and phosphonooxy groups in some bonding form (as such, the group Y is hereafter referred to as "polar group-modified hydrocarbon group Y").

Also, the polar group-modified hydrocarbon group Y may have a further substituent group or a different bonding present in the hydrocarbon, if desired, including, for example, a hydroxyl group, a halogen atom, a nitrile group, an imidazole group, an amide bond, an ether bond, an ester bond, a urethane bond, a thioether bond, or a disulfide bond.

When X is a group represented by the formula —CO—Y or the formula -Y in the formula (II), the hydrocarbon portion of the polar group-modified hydrocarbon group Y may be any one of saturated or unsaturated hydrocarbon groups, but preferably, the hydrocarbon group is an alkylene group, an arylene group or a cycloalkylene group, having 1 to 18 carbon atoms, more preferably having 1 to 10 carbon atoms. More specifically, the hydrocarbon group in the polar group-modified hydrocarbon group Y includes, for example, alkylene groups such as methylene, ethylene, trimethylene, butylene, pentylene, hexylene, heptylene, and octylene; di-valent aromatic hydrocarbon groups such as phenylene and naphthylene; and di-valent cycloaliphatic hydrocarbon groups such as cyclohexylene. Particularly, "Y" is preferably a lower alkylene group such as methylene, ethylene, propylene, and butylene, with respect to ready production of the polyvinyl alcohol in accordance with the present invention.

In the structural formula (II), the group X may form a phosphonooxy group along with the oxygen atom to which X is bonded, and in such case, the structural unit (II) has a structure where the phosphonooxy group is directly bonded to the carbon atom composing the main chain of the polyvinyl alcohol.

The structural unit (II) includes, with no specific limitation, structural units represented by the following chemical formulas:

The structural unit (II) wherein X has a carboxyl group-modified hydrocarbon group Y or a group represented by the formula —CO—COOH, includes, for example, structural units represented by the following chemical formulas (IIa-1) to (IIa-8).

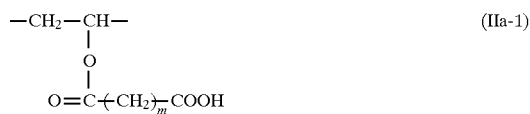

"m" is an integer of 0 to 18, preferably 2 to 10, and more preferably 2 to 4.

"n" is an integer of 1 to 18, preferably 1 to 10, and more preferably 1 to 4.

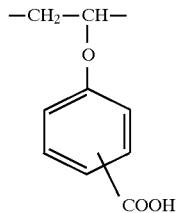 (IIa-5)

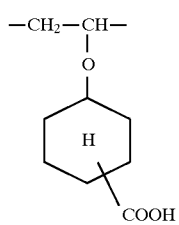 (IIa-6)

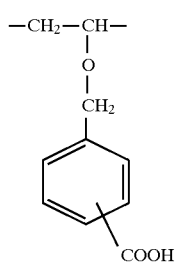 (IIa-7)

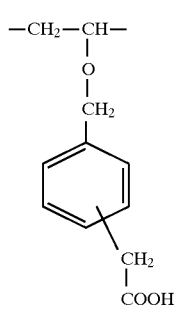 (IIa-8)

The structural unit (II) wherein X has a sulfo group-modified hydrocarbon group Y, includes, for example, structural units represented by the following chemical formulas (IIb-1) to (IIb-10).

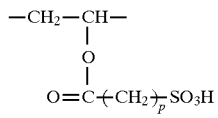 (IIb-1)

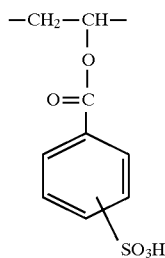 (IIb-2)

"p" is an integer of 1 to 18, preferably 1 to 10, and more preferably 1 to 4.

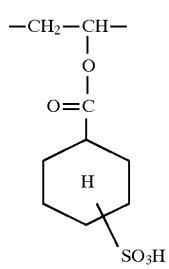 (IIb-3)

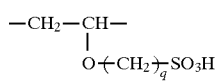 (IIb-4)

"q" is an integer of 1 to 18, preferably 1 to 10, and more preferably 1 to 4.

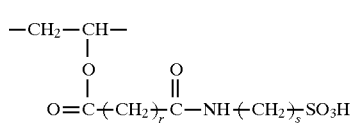 (IIb-5)

"r" and "s" are independently an integer of 1 to 18, preferably 1 to 10, and more preferably 1 to 4.

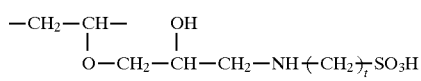 (IIb-6)

"t" is an integer of 1 to 18, preferably 1 to 10, and more preferably 1 to 4.

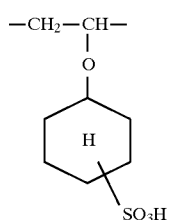 (IIb-7)

 (IIb-8)

 (IIb-9)

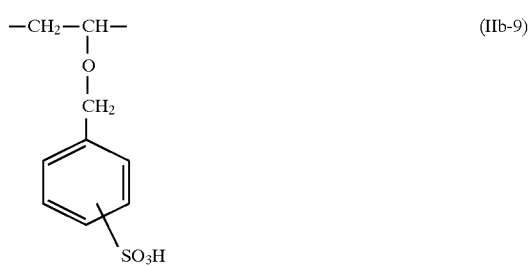

(IIb-10) 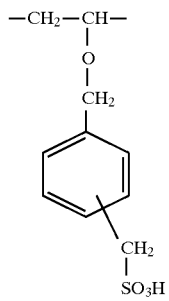

The structural unit (II) wherein X has an amino group-modified hydrocarbon group Y, includes, for example, structural units represented by the following chemical formulas (IIc-1) to (IIC-10).

(IIc-1) 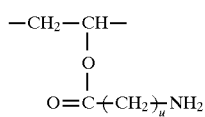

"u" is an integer of 1 to 18, preferably 1 to 10, and more preferably 1 to 4.

(IIc-2) 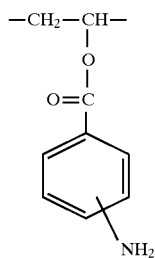

(IIc-3) 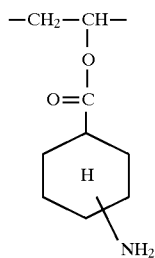

(IIc-4) 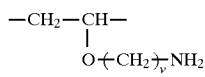

"v" is an integer of 1 to 18, preferably 1 to 10, and more preferably 1 to 4.

(IIc-5) 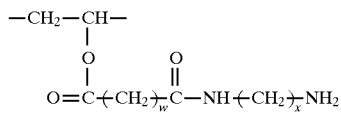

"w" and "x" are independently an integer of 1 to 18, preferably 1 to 10, and more preferably 1 to 4.

(IIc-6) 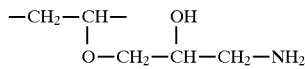

(IIc-7) 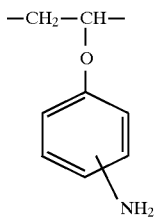

(IIc-8) 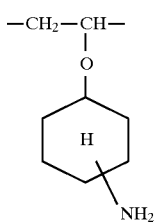

(IIc-9) 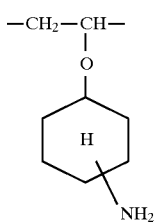

(IIc-10) 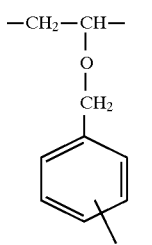

The structural unit (II) wherein X has a phosphonooxy group-modified hydrocarbon group Y or X forms a phosphonooxy group together with the oxygen atom to which X is bonded, includes, for example structural units represented by the following chemical formulas (IId-1) to (IId-3).

(IId-1) 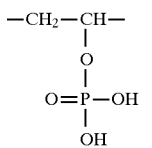

(IId-2) 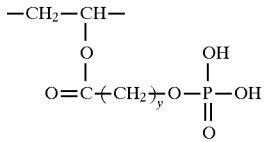

"y" is an integer of 1 to 18, preferably 1 to 10, and more preferably 1 to 4.

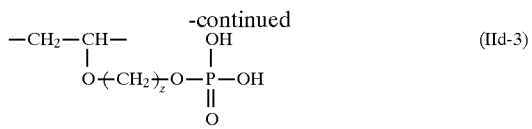

"z" is an integer of 1 to 18, preferably 1 to 10, and more preferably 1 to 4.

In addition to the above exemplified groups of structural unit (II), the structural unit (II) may be a group represented by the formula —CO—Y or the formula -Y wherein the group Y is a polar group-modified hydrocarbon group having two or more substituents selected from carboxyl, sulfo, amino and phosphonooxy groups.

Additionally, the polyvinyl alcohol of the present invention can contain within the main chain one or more different structural units of formula (II).

In accordance with the present invention, the structural unit (II) in the polyvinyl alcohol is preferably any one of the structural units represented by the chemical formulas (IIa-1), (IIa-4), (IIb-1), (IIb-4), (IIb-5), (IIb-6), (IIc-1), (IIc-4), (IIc-5), (IIc-6), (IId-1), (IId-2), and (IId-3), with respect to ready production of the polyvinyl alcohol and the properties of the resulting polymer.

In the polyvinyl alcohol of the present invention, the structural unit (I) is a structural unit represented by the chemical formula (Ia) and/or chemical formula (Ib), and the structural unit (II) is more preferably at least one of the structural units represented by the chemical formula (IIa-1) with "m" of 2 to 4; (IIa-4) with "n" of 1 to 4; (IIb-1) with "p" of 1 to 4; (IIb-4) with "q" of 1 to 4; (IIb-5) with "r" and "s", both of 1 to 4; (IIb-6) with "t" of 1 to 4; (IIc-1) with "u" of 1 to 4; (IIc-4) with "v" of 1 to 4; (IIc-5) with "w" and "x", both of 1 to 4; (IIc-6); (IId-1); (IId-2) with "y" of 1 to 4; and (IId-3) with "z" of 1 to 4. The gel from such a polyvinyl alcohol can attain even further improved flexibility, transparency, resistance to moist heat, resistance to hot water, water absorptivity, occlusiveness and ready preparation.

The polyvinyl alcohol of the present invention should necessarily contain a 0.05 to 0.50 molar fraction, preferably a 0.10 to 0.40 molar fraction, of the structural unit (I) relative to the total structural units composing the main chain of the polyvinyl alcohol. If the molar fraction of the structural unit (I) in the polyvinyl alcohol is below 0.05, the gel formed from the polyvinyl alcohol cannot have sufficient strength and is not practically durable because of the deteriorated resistance to hot water or the decrease of transparency. Therefore, such a polymer cannot be effectively used for the variety of applications as described above, including wound dressing materials.

If the molar fraction of the structural unit (I) in the polyvinyl alcohol is above 0.50, on the contrary, the solvent content (such as the water content) in the gel formed from the polyvinyl alcohol is decreased, also causing a decrease in the flexibility and transparency of the polyvinyl alcohol.

The molar fraction of the structural unit (I) in the polyvinyl alcohol of the present invention can be analyzed by $^1$H-NMR.

In accordance with the present invention, the polyvinyl alcohol should necessarily contain the structural unit (II) at a molar fraction of 0.0001 to 0.50, and the polymer preferably contains the structural unit (II) at a molar fraction satisfying the following formula (1);

$$\{(1-C_{est}) \times C_{est}\} \times 0.01 \leq C_{pol} \leq \{1-C_{est}) \times C_{est}\} \times 2.0 \tag{1}$$

wherein $C_{pol}$ is the molar fraction of the structural unit (II); and $C_{est}$ is the molar fraction of the structural unit (I). More preferably, the polymer contains the structural unit (II) within a range satisfying the formula (3);

$$\{(1-C_{est}) \times C_{est}\} \times 0.05 \leq C_{pol} \leq \{1-C_{est}) \times C_{est}\} \times 1.0 \tag{3}$$

wherein $C_{pol}$ and $C_{est}$ are the same as described above.

If the molar fraction of structural unit (II) in the polyvinyl alcohol is below 0.0001, the transparency and flexibility of the gel formed from the polyvinyl alcohol is insufficient, while if the molar fraction $C_{pol}$ of the structural unit (II) is above 0.50, the resistance to hot water of the gel formed from the polyvinyl alcohol is decreased. The molar fraction of structural unit (II) in the polyvinyl alcohol may be determined by $^1$H-NMR or potentiometric titration in an aqueous solvent. Because quantitative $^1$H-NMR analysis of signals in polymers may often be inaccurate due to the constrained local motion of molecular chains, depending on the selected solvent, the molar fraction of the structural unit (II) is preferably determined more accurately by potentiometric titration in an aqueous solvent.

In order to further improve the transparency and water resistance of the gel formed from the polyvinyl alcohol of the present invention, the average chain length ($L_{est}$) of structural unit (I), represented by the following formula (2);

$$L_{est} = (C_{est}/C_{met}) \times 2 \tag{2}$$

wherein $C_{est}$ represents the molar fraction of structural unit (I); $C_{met}$ represents the molar fraction of the methylene carbon interposed between the methine carbon bonded with a hydroxyl group or a group represented by the formula —OX and the methine carbon composing the structural unit (I) among the methylene carbons composing the main chain of the polyvinyl alcohol; is preferably 2.0 or more, more preferably 3.0 or more and most preferably 4.0 or more.

The content of the average chain length ($L_{est}$) will now be described below.

As is shown in the following chemical formula (III),

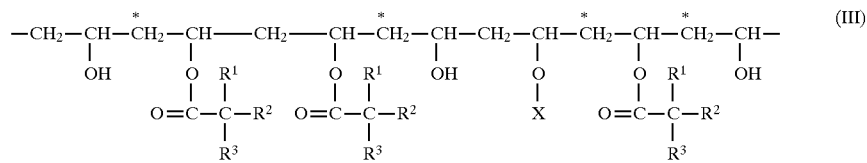

wherein $R^1$, $R^2$, $R^3$ and X are as described above, the partial structure of the polyvinyl alcohol of the present invention is in a form wherein the vinyl alcohol unit and the structural units (I) and (II) are bonded together. Herein, the term "$C_{met}$" means the molar fraction of the methylene carbon (carbon marked with * in the chemical formula (III)), which is interposed between the methine carbon (namely, a group —CH(OH)— or a group —CH(OX)—) bonded with the hydroxyl group or a group represented by the formula —OX and the methine carbon (namely, a group —CH—O—CO—C($R^1$)($R^2$)($R^3$)-) composing the structural unit (I), among the methylene carbons (—CH$_2$—) composing the main chain of the polyvinyl alcohol, with respect to all the structural units of the polyvinyl alcohol.

As a plurality of the structural units (I) are more closely present and adjacent to each other with no separation through any vinyl alcohol unit or the structural unit (II) in the polyvinyl alcohol, the number of the methylene carbons marked * within the chemical structure formula (III) is smaller, involving a smaller molar fraction $C_{met}$ thereof [smaller than the molar fraction of the structural unit (I)]. Consequently, the average chain length ($L_{est}$) of the structural unit (I) represented by the formula (2) gradually increases to be larger than 1.

In the polyvinyl alcohol of the present invention, the average chain length ($L_{est}$) of the structural unit (I) is preferably 2 or more. Therefore, the ratio of a plurality of the structural units (I) present closely and adjacent to each other is preferably larger in the polyvinyl alcohol.

In the polyvinyl alcohol where a plurality of the structural units (I) are never adjacent to each other so the units are totally separated from each other while interposing vinyl alcohol units and the structural unit (II) in between the units (I), the $C_{met}$ is 2-fold the molar fraction of the structural unit of the structural unit (I), while the average chain length ($L_{est}$) of the structural unit (I), represented by the formula (2), is equal to 1. Herein, the $C_{met}$ can be determined by $^{13}$C-NMR of the polyvinyl alcohol.

With respect to improving the resistance of the gel to hot water, the syndiotacticity of the polymer should be 55% or more, more preferably 58% or more and most preferably 60% or more, by diad tacticity representation. Herein, the term "diad tacticity representation" means diad tacticity representation determined by a process comprising completely saponifying the polyvinyl alcohol, dissolving the completely saponified product in dimethylsulfoxide, and determining the triad tacticity from the hydroxyl proton signal on the proton NMR spectrum of the resulting solution, and calculating the diad tacticity from the syndiotacticity and heterotacticity in the triad tacticity by the following formula (4);

$$\text{diad tacticity} = S + (H/2) \quad (4)$$

wherein S and H represent syndiotacticity and heterotacticity, respectively, in the triad tacticity determined from proton NMR.

With respect to mechanical strength, resistance to hot water and processability of the gel formed from the polyvinyl alcohol of the present invention, the viscosity average polymerization degree of the polyvinyl alcohol should be 300 or more, preferably 800 or more, and more preferably 1500 or more. With respect to the processability of the gel formed from the polyvinyl alcohol, additionally, the viscosity average polymerization degree of the polymer is preferably 50,000 or less. The term "viscosity average polymerization degree" herein referred to means a value determined by a process comprising completely saponifying the polyvinyl alcohol, totally acetylating the completely saponified product to recover polyvinyl acetate, measuring the intrinsic viscosity η (dl/g of the polyvinylacetate in acetone at 30° C. and calculating the value by the following formula (5);

$$P = \{[\eta] \times (1000/7.94)\}^{(1/0.62)} \quad (5)$$

wherein "P" represents the viscosity average polymerization degree of polyvinyl alcohol.

In order to prepare a flexible gel from the polyvinyl alcohol, the polymer should have a lower degree of crystallinity. Generally, the crystallinity of a polyvinyl alcohol is decreased as the melting point of the polymer is lowered. To improve the flexibility of the gel formed from the polyvinyl alcohol, the polyvinyl alcohol should have a melting point of preferably 200° C. or less, and more preferably 180° C. or less. The melting point of the polyvinyl alcohol is determined by pulverizing the polymer and measuring the endothermic peak temperature in nitrogen atmosphere under the condition of a temperature elevation rate of 10° C./min by differential scanning thermal analysis.

Along with the vinyl alcohol unit and the structural units (I) and (II), the polyvinyl alcohol of the present invention may contain other structural units, if necessary, so long as the objects of the present invention are not disrupted. Such other structural units include for example, vinyl esters such as vinyl acetate, vinyl formate, vinyl propionate, vinyl valerate, vinyl caprate, and vinyl laurate; olefins such as ethylene, propylene, isobutylene, α-octene, and α-dodecene; α,β-unsaturated carboxylic acids such as (meth)acrylic acid, crotonic acid, maleic anhydride, and itaconic acid and the esters and salts thereof; unsaturated nitriles such as acrylonitrile and methacrylonitrile; unsaturated amides such as (meth)acrylamide and N-vinylpyrrolidone; olefin sulfonic acid such as ethylene sulfonic acid, allyl sulfonic acid, and methacryl sulfonic acid, and the salts thereof; unsaturated ethers such as isopropyl vinyl ether; and units derived from polymerizable monomers such as halogenated olefins including vinyl chloride and vinylidene chloride. The molar fraction of other structural units described above should preferably be 0.1 or less, on the basis of the total structural units of the polyvinyl alcohol.

Depending on the use, the hydroxyl group of the polyvinyl alcohol of the present invention may be chemically modified. Further, the transparency, flexibility, and physical and mechanical strength thereof may be modified by modifying and adjusting the molar fractions of the structural units (I) and (II) and/or the chain length $L_{est}$ of the structural unit (I) in the polyvinyl alcohol within the scope of the present invention. Thus, properties such as pharmaceutical agent release functions may be imparted to a wound dressing material comprising the polyvinyl alcohol, by adjusting the physico-chemical properties of the polymer.

The polyvinyl alcohol of the present invention may be produced by any process, with no limitation, as long as the requirements (i) and (ii) are satisfactorily met. For example, the polyvinyl alcohol may be produced by any of the following processes 1–4:

Process 1 for Producing the Polyvinyl Alcohol of the Present Invention

By simultaneously or sequentially modifying polyvinyl alcohol produced by routine methods by using a carboxylic acid represented by the following formula (IV)

$$H—O—CO—C(R^1)(R^2)(R^3) \quad (IV)$$

wherein $R^1$, $R^2$ and $R^3$ represent the same groups as described above and/or an ester-forming derivative thereof (referred to as "carboxylates (IV)" hereinbelow), a compound represented by the following formula (V)

$$Z-X \quad (V)$$

wherein X represents the same group as described above; and Z represents hydroxyl group or halogen (referred to as "compound (V)" hereinbelow), an ester-forming derivative thereof and/or an ether-forming derivative thereof, the structural units (I) and (II) can be incorporated at given molar fractions in the polyvinyl alcohol.

Process 2 of Producing the Polyvinyl Alcohol of the Present Invention

Using one or more vinyl ester compounds represented by the following formula (VI)

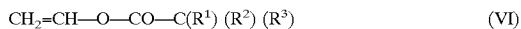

$$CH_2=CH-O-CO-C(R^1)(R^2)(R^3) \quad (VI)$$

wherein $R^1$, $R^2$ and $R^3$ represent the same groups as described above (referred to as "vinyl ester compound (VI)" hereinbelow) for addition polymerization, a homopolymer or a copolymer, containing one or more different structural units (I) as the repeating unit, is produced. Otherwise, copolymerizing the vinyl ester compound (VI) with another vinyl ester compound, such as, vinyl trifluoroacetate, vinyl trichloroacetate, vinyl formate, or vinyl acetate, and/or a vinyl ether compound, such as t-butyl vinyl ether or trimethylsilyl vinyl ether, a copolymer comprising a unit derived from the structural unit (I) and the vinyl ester compound and/or the vinyl ether compound, is produced.

The homopolymer or copolymer thus produced is partially saponified to leave a 0.05–0.50 final molar fraction of the structural unit (I) in the saponified product.

Then, the hydroxyl group of the saponified product produced by saponification is modified to a final 0.0001 to 0.50 molar fraction range of the structural unit (II) in the final polyvinyl alcohol, by using compound (V) represented by formula (V), the ester-forming derivative and/or ether-forming derivative thereof.

Process 3 of Producing the Polyvinyl Alcohol of the Present Invention

Using one more vinyl ester compounds described above in Process 2, a homopolymer or a copolymer, containing one or more different structural units (I) as the repeating unit, is produced, or by copolymerizing the vinyl ester compound (VI) with another vinyl ester compound, such as vinyl trifluoroacetate, vinyl trichloroacetate, vinyl formate, or vinyl acetate, and/or a vinyl ether compound, such as t-butyl vinyl ether or trimethylsilyl vinyl ether, a copolymer comprising a unit derived from structural unit (I) and the vinyl ester compound and/or the vinyl ether compound, is produced.

The homopolymer or copolymer thus produced is then partially saponified to leave a 0.05–0.50 final molar fraction of structural unit (I) in the saponified product.

Then, the hydroxyl group of the saponified product is allowed to react with an epoxy group-containing compound, such as epihalohydrin, to introduce the epoxy group into the side chain of the homopolymer or the copolymer.

Thereafter, the epoxy group in the modified polymer is allowed to react with a compound having a group reactive with an epoxy group and also having at least one polar group selected from the group consisting of carboxyl, sulfo, amino and phosphonooxy groups (such as aminoalkyl sulfonic acid, diamino alkanes, ammonia, dicarboxylic acids, a compound with a hydroxyl group and a carboxyl group, a compound with an amino group and a carboxyl group, or phosphoric acid) to form a structural unit (II) with a polar group-modified hydrocarbon group Y incorporating one or more carboxyl, sulfo, amino or phosphonooxy groups, wherein the molar fraction of structural unit (II) in the final polyvinyl alcohol is adjusted within a range of 0.0001 to 0.50.

Process 4 of Producing the Polyvinyl Alcohol of the Present Invention

Using one or more of the vinyl ester compounds for addition polymerization described in Process 2, a homopolymer or a copolymer, containing one or more different structural units (I) as the repeating unit, is produced; or by copolymerizing vinyl ester compound (VI) with another vinyl ester compound (such as, vinyl trifluoroacetate, vinyl trichloroacetate, vinyl formate or vinyl acetate) and/or a vinyl ether compound (such as, t-butyl vinyl ether or trimethylsilyl vinyl ether), a copolymer comprising a unit derived from structural unit (I) and the vinyl ester compound and/or the vinyl ether compound, is produced.

The homopolymer or copolymer thus produced is partially saponified to leave a 0.05–0.50 final molar fraction of structural unit (I) in the saponified product.

Then, the hydroxyl group of the saponified product is allowed to react with a dicarboxylic anhydride having a ring structure, such as succinic anhydride, glutaric anhydride and phthalic anhydride; or a carboxylic acid having a halogen, such as chloroacetic acid, chloropropionic acid, bromoacetic acid, and iodoacetic acid, to introduce the carboxyl group into the side chain of the homopolymer or the copolymer.

Thereafter, the polymer with carboxyl group introduced into the side chain thereof, is allowed to react with a compound having a group reactive with a carboxyl group (such as an amino group, a hydroxyl group or an acid halide group) etc.) and having a carboxyl group, a sulfo group, or an amino group and/or a phosphonooxy group (such as aminoalkyl sulfonic acids, diaminoalkanes, amino acids, hydroxycarboxylic acids, and phosphonooxy group containing compounds) to form a structural unit (II) having a hydrocarbon group Y modified with at least one polar group selected from carboxyl, sulfo, amino and phosphonooxy groups, wherein the molar fraction of structural unit (II) in the final polyvinyl alcohol is adjusted within a range of 0.0001 to 0.50.

The compound (V), its ester-forming derivative or ether-forming derivative, used in Processes 1 and 2, include, with no specific limitation, dicarboxylic acids such as oxalic acid, malonic acid, succinic acid, glutaric acid and phthalic acid; dicarboxylic anhydrides with a ring structure, such as succinic anhydride, glutaric anhydride and phthalic anhydride; carboxylic acids with halogen substituents, such as chloroacetic acid, chloropropionic acid, bromoacetic acid, and iodoacetic acid; phosphoric acid, phosphoric anhydride, phosphorus oxide, and phosphorus chloride; sulfonic acid compounds with halogen substituents; and amine compounds with halogen substituents. These compounds may be used singly or as a combination of two or more.

The vinyl ester compound (VI) used in Processes 2 to 4 includes, with no specific limitation, vinyl trialkylacetates such as vinyl pivalate, vinyl dimethylethylacetate, vinyl dimethylpropylacetate, vinyl diethylmethylacetate, vinyl triethylacetate, vinyl tripropylacetate, and vinyl versatate; vinyl dialkylacetates such as vinyl dimethylacetate, vinyl diethylacetate, and vinyl dipropylacetate; vinyl esters with cyclic hydrocarbon groups, such as vinyl methylcyclohexylacetate, vinyl 1-norbornanecarboxylate, and vinyl 3-noradamantanecarboxylate. The vinyl ester compounds (VI) can be used singly or in a combination of two or more.

In Process 1 described above, polyvinyl alcohol is simultaneously or sequentially modified by using carboxylic acids (IV) and compounds (V) under the same conditions as those conventionally adopted for esterification or etherification of the hydroxyl group of polyvinyl alcohol. With no specific limitation, for example, the polyvinyl alcohol with structural units (I) and (II) of the present invention can be produced by simultaneously or sequentially reacting the carboxylic acids (IV) and the compound (V) with polyvinyl alcohol dissolved in an appropriate solvent (such as dimethylsulfoxide, dimethylformamide, water, or a mixture thereof) at a temperature of 50° to 150° C.

To produce the polyvinyl alcohol of the present invention by Processes 2 to 4, vinyl ester compound (VI) is polymerized together with smaller amounts of other polymerizable monomers described above, if necessary, in the presence of an appropriate polymerization initiator, by mass polymerization, solution polymerization, suspension polymerization, emulsion polymerization and the like at a temperature within a range of −80° to 300° C., preferably from −50° to 250° C., more preferably from 0° to 100° C., to produce a homopolymer comprising the structural unit (I) or a copolymer primarily comprising the structural unit (I). If the process is carried out at about 0° to 100° C., then, a polyvinyl alcohol with a syndiotacticity above 55% by diad tacticity representation can be produced in a smooth manner, preferably. Then, preferably in the absence of oxygen or in the presence of an antioxidant, the polymer is saponified while the polymer is preferably dissolved in an organic solvent (such as ethers, ketones, amides, sulfoxides, aromatic hydrocarbons, alcohols and mixtures thereof). The saponification is generally performed at a temperature of about 40° to 70° C. by using a base, including, but not limited to, alkali metal hydroxides, such as potassium hydroxide and sodium hydroxide, and alkali metal alkoxides, such as potassium methoxide, potassium ethoxide, potassium t-butoxide, sodium methoxide, and sodium ethoxide. The saponification is performed to give a final molar fraction of the structural unit (I) in the polyvinyl alcohol of from 0.05 to 0.50 as described above (Processes 2 to 4) (see also U.S. Pat. No. 5,187,226 for additional details regarding this process, the content of which is hereby incorporated by reference).

After recovering the saponified product, further steps should be carried out while retaining the molar fraction of structural unit (II) in the polyvinyl alcohol within the range of 0.0001 to 0.50. Furthermore, these later steps should preferably be carried out at a temperature of about 50° to 120° C., by using the same organic solvents as those used in saponification.

Before gelation, the polyvinyl alcohol of the present invention containing specific molar fractions of the structural units (I) and (II), as described above, is generally in the form of dry powder or a powder containing water or an organic solvent.

For forming a gel from the polyvinyl alcohol of the present invention, the gel may be prepared as a hydrogel, a gel in an organic solvent, or a gel in a solvent mixture of water and an organic solvent, depending on the use of the prepared gel. Among these, a hydrogel is very effective because it can be applied to a wide variety of uses. Hydrogels may be prepared by any conventional method, with no specific limitation. One example of a method for preparing a hydrogel is described below.

A transparent hydrogel, in the form of, for example, a plate, a tube, a mass, a fiber or particulates is prepared by dissolving the polyvinyl alcohol of the present invention in an aqueous organic solvent to give a solution with a final concentration of 0.1 to 50% by weight, preferably 1 to 20% by weight, and subjecting the solution to a process selected from: (1) pouring onto a mold plate, such as glass plate, (2) charging into a mold such as a glass tube, (3) extruding from a T-die into a film, (4) spinning, or (5) preparation into micro-droplets. The resulting product is then immersed and gelatinized in water, an aqueous organic solvent, or a mixture of water and an aqueous organic solvent, and subsequently the gelatinized product is immersed in a solvent including water. In such case, the aqueous solvent dissolving the polyvinyl alcohol may be any organic solvent capable of dissolving the polyvinyl alcohol and soluble in water, including, but not limited to, dimethylsulfoxide, N-methylpyrrolidone, 1,1,1,3,3,3-hexafluoro-2-propanol, dimethylformamide, dimethylacetamide, glycerine, and ethylene glycol. These solvents may be used singly or as a combination of two or more. In some cases, a small amount of an inorganic salt (such as lithium chloride, zinc chloride, or sodium nitrate) can be added to the solvent for improving the solubility.

For forming a gel from the polyvinyl alcohol, processes may be selected from: (1) cross-linking with radiation and peroxides, (2) cooling of the solution with the polyvinyl alcohol dissolved therein, (3) freezing of the solution, and (4) repetition of freezing and thawing of the solution.

Depending on the use, the gel of the present invention, particularly a hydrogel, may be prepared in any desired form such as powder (fine particle), film, sheet, fiber, woven knit, non-woven fabric, tube, in a mass or thin slice. For use as a wound dressing material, the gel may be used in the form of powder (fine particle), film, sheet, fiber, woven knit, non-woven fabric, net, tube and the like.

To adjust the water content or the adhesiveness and/or depending on their use, the gel of the present invention, particularly hydrogel, may contain other components, during and after the production of the gel. Any other conventional component may be used, with no specific limitation, as long as the component does not suppress the gelation or does not disturb the properties such as gel strength, transparency, and flexibility. Suitable examples of other components that can be added include polysaccharides such as alginic acid and chitosan; polyamino acids such as polylysine, polyaspartic acid, and polyglutamic acid; proteins such as collagen, albumin, and gelatin; synthetic polymers such as polyacrylic acid, polymethacrylic acid, ethylene-vinyl alcohol copolymer, polyvinyl acetate, and polyethylene glycol; low molecular compounds such as ethylene glycol, glycerine, succinic acid and oxalic acid; and derivatives thereof.

The form or shape of the gel of the present invention, particularly hydrogel for use as wound dressing materials is with no specific limitation, and these gels may be used like conventionally known gels for wound dressing materials. The wound dressing material of the present invention may satisfactorily contain pharmaceutically acceptable, conventional additives including a softening agent and a stabilizer such as glycerine and polyethylene glycol or may satisfactorily contain pharmaceutical agents and biologically active substances with activities effective for wound healing, including divalent metal ions having pharmacological activity such as $Ca^{2+}$, disinfectants, anti-bacterial agents such as antibiotics, blood circulation improving agents such as PGE1, growth factors such as TGF β, PDGF, and FGF, enzyme inhibitors such as urinastatin and TIMP, and steroidal or non-steroidal anti-inflammatory agents. The aforementioned agents and biologically active substances can be immobilized onto the gel used as a wound dressing material via an appropriate spacer or a linker to be cleaved in response to stimulus.

The gel of the present invention, particularly hydrogel, has excellent resistance to hot water with less solubilized matter, even if the gel is processed in hot water at high temperatures. Thus, the gel has low toxicity. Additionally, the gel has such good resistance to moist heat that the gel can retain its excellent properties even after the gel is steam sterilized at a high temperature of 121° C. for 20 minutes. Furthermore, the gel has such superior water absorptivity and occlusiveness that the gel can absorb and retain exudate from wounds. Therefore, the gel can sufficiently exert its effects when used as a wound dressing material.

The gel from the polyvinyl alcohol of the present invention, particularly hydrogel, has excellent flexibility and transparency, and also has good resistance to moist heat and resistance to hot water, durability to steam sterilization and boiling in water, and additionally, the gel has good water absorptivity and occlusiveness. Thus, the gel of the present invention can effectively be used as a wound dressing material, gel for immobilizing enzymes and bacteria, contact lens, artificial muscle, artificial cartilage, artificial joint, artificial organ, sensor, functional separation membrane, release control membrane, switch, actuator, or micromachine.

A wound dressing material comprising the polyvinyl alcohol of the present invention will not be modified even after steam sterilization at 121° C. for 20 minutes, will contain less solubilized matter and will thus be much safer. The wound dressing material of the present invention is highly transparent, so the conditions of wound sites, such as the presence or absence of bacterial infection and the appearance of dermal or epidermal cells in growth, can be observed through the wound dressing material attached on the wound sites. Additionally, the gel is so highly flexible that the gel attached on wound sites can reduce extraneous irritation with less pain for patients. Because the wound dressing material of the present invention has excellent water absorptivity and occlusiveness, the material can also absorb and retain body fluid tightly enough to exert a function of controlling the vaporization of water. Thus, the material can exhibit an excellent healing promoting effect as an occlusive wound dressing material. Also, the wound dressing material of the present invention has a reactive hydroxyl group, so the material can be chemically modified if desired. Additionally, the properties of the present material can be controlled by adjusting the molar fractions of the structural units (I) and (II) in the polyvinyl alcohol composing the wound dressing material. Thus, the material can be further improved to give a wound dressing material, for example as a wound dressing material provided with a pharmaceutical agent release function.

EXAMPLES

Having generally described this invention, a further understanding can be obtained by reference to certain specific examples which are provided herein for purposes of illustration only and are not intended to be limiting unless otherwise specified.

Example 1

Into a reaction vessel with an agitator were charged vinyl pivalate (200 g) and methanol (70 g), and the whole reaction system was purged with nitrogen gas. Meanwhile, 2,2'-azobisisobutylonitrile (0.04 g) as a polymerization initiator was dissolved in methanol (5 g), and the resulting solution was purged with nitrogen gas. The temperature of the reaction vessel was elevated until the inner temperature reached 60° C. Then, the solution of the polymerization initiator prepared above was added into the vessel for initiating polymerization and the polymerization carried out for 5 hours while keeping the vessel at the same temperature, until the polymerization ratio reached 40%. Then, the reaction system was cooled to 20° C. for terminating polymerization. While gradually adding t-butanol to the system, unreacted vinyl pivalate was removed under reduced pressure to recover polyvinyl pivalate in t-butanol solution, to which was added an appropriate amount of tetrahydrofuran to distill t-butanol under reduced pressure, to recover a solution of polyvinyl pivalate in tetrahydrofuran (at a concentration of 45.7% by weight).

Into a reaction vessel with an agitator and a reflux condenser was charged the solution of polyvinyl pivalate in tetrahydrofuran (50 g) produced above. The resulting mixture was heated to 60° C. and then purged with nitrogen gas. While keeping the reaction vessel at 60° C., an aqueous 25% potassium hydroxide solution (20 g), prepared preliminarily and purged with nitrogen gas, was added into the vessel prior to thorough agitation. The reaction system was gelatinized over about 30 minutes. While maintaining the reaction system at 60° C. for another 60 minutes, acetic acid (5.5 g) and methanol (5.5 g) were added to the reaction system to neutralize the potassium hydroxide. After pulverizing the gel, washing with methanol in a Soxhlet extractor was conducted to recover a partially saponified polyvinyl alcohol containing the structural unit (I).

The molar fraction of the structural unit (I) and the molar fraction of the vinyl alcohol unit in the partially saponified polyvinyl alcohol containing the structural unit (I), were determined by the following method. The molar fraction of the structural unit (I) and that of the vinyl alcohol unit were 0.19 and 0.81, respectively.

Determination of the Molar Fraction of the Structural Unit (I) and the Molar Fraction of the Vinyl Alcohol Unit The partially saponified polyvinyl alcohol (0.01 g) containing the structural unit (I), was dissolved in a mixture of $d_6$-dimethylsulfoxide (1.0 g) and deutero-chloroform (0.2 g). $^1$H-NMR was conducted by an NMR system manufactured by Nippon Denshi, Co. Ltd. (JNM-GSX 270), to determine the molar fraction of the structural unit (I) and the molar fraction of the vinyl alcohol unit in the polyvinyl acetate (namely, polyvinyl alcohol).

The viscosity average polymerization degree of the partially saponified polyvinyl alcohol containing the structural unit (I), was 1650, as determined by the following method.

Determination of Viscosity Average Polymerization Degree of Polyvinyl Alcohol

The partially saponified polyvinyl alcohol (2 g) containing the structural unit (I), was dissolved in methanol (10 g), to which was then added potassium hydroxide (1.6 g). The resulting mixture was heated at 60° C. for 120 minutes, to completely saponify the ester bonds in the polyvinyl alcohol including the structural unit (I). To the resulting completely saponified polyvinyl alcohol (1 g) were added acetic anhydride (30 g) and pyridine (6 g) prior to sealing. Subsequently, the hydroxyl groups in the polyvinyl alcohol were completely acetylated while heating the resulting mixture at 110° C. for 5 hours, followed by addition of n-hexane to precipitate the polyvinyl acetate generated by acetylation. Then, a process of dissolution of the precipitate in acetone and subsequent precipitation with n-hexane was twice repeated for purification. The resulting purified polyvinyl acetate (0.4 g) was dissolved in acetone (80 g) to determine the intrinsic viscosity η at 30° C.

Then, the viscosity average polymerization degree was determined by the aforementioned formula (5).

The syndiotacticity of the partially saponified polyvinyl alcohol, was 61% by diad tacticity representative as determined by the following method and in accordance with the aforementioned formula (4).

Determination of Syndiotacticity

The purified polyvinyl alcohol (0.01 g) used for determination of viscosity average polymerization degree as described above was dissolved in $d_6$-dimethylsulfoxide (1 g). Then, the syndiotacticity and heterotacticity in the triad tacticity was determined from the hydroxyl proton signal on the $^1$H-NMR spectrum of the resulting solution, by an NMR system manufactured by Nippon Denshi, Co. Ltd. (Type JNM-GSX 270). By the aforementioned formula (4), syndiotacticity by diad tacticity representation was determined, which was designated the syndiotacticity of the partially saponified polyvinyl alcohol containing the structural unit (I).

The partially saponified polyvinyl alcohol (10 g) containing the structural unit (I) was dissolved in dimethylsulfoxide (190 g), to which were added succinic anhydride (0.41 g) and pyridine (0.32 g) for reaction at 110° C. for one hour. The resulting solution, weighing about 200 g, was poured onto a polystyrene tray (240-mm length×240-mm width), and the solution on the tray was immersed overnight in water at 25° C. for gelation. The resulting gel was washed sufficiently in water, and the gel was then immersed in isotonic sodium chloride solution to substitute water therein with isotonic sodium chloride solution, to recover a transparent sheet-type hydrogel (about 240-mm length×240-mm width× 3.5-mm thickness) with excellent flexibility.

By the following methods, determination and assessment were made of the hydrogel and the polyvinyl alcohol composing the hydrogel, concerning the molar fraction of the structural unit (II), the average chain length ($L_{est}$) of the structural unit (I), water content, endothermic peak temperature, resistance to hot water, handleability, flexibility, transparency, water absorption ratio, and the amount of solubilized matters. The results are shown in the following Table 1.

Molar Fraction of the Structural Unit (II) in the Hydrogel

The hydrogel (2.26 g) was ground and dispersed in 0.02N hydrochloric acid (5 ml) and pure water (10 ml). The resulting dispersion was titrated, under stirring, with an aqueous 0.01N sodium hydroxide solution, to determine the content ($\mu$mol) of carboxyl groups in the hydrogel on the basis of the relation between the amount of the sodium hydroxide solution required for titration and pH. Based on the results, the molar fraction of the structural unit (II) in the polyvinyl alcohol composing the hydrogel was determined.

Average Chain Length ($L_{est}$) of the Structural Unit (I) in the Polyvinyl Alcohol The hydrogel was heated at 110° C. for 6 hours to completely remove the water from the gel. The resulting polyvinyl alcohol was ground. The ground polyvinyl alcohol (1.0 g) was dissolved in $d_6$-dimethylsulfoxide/deuterochloroform (=5:1 in w/w; 10 ml), and $^{13}$C-NMR of the resulting solution was analyzed by JNM-GSX 270 manufactured by Nippon Denshi, Co. Ltd., to determine the $C_{met}$, namely the molar fraction of the methylene carbon interposed between the methine carbon composing the structural unit (I) in the polyvinyl alcohol and the methine carbon bound with a hydroxyl group or a group represented by the formula —OX. By the aforementioned formula (2), the average chain length ($L_{est}$) of the structural unit (I) was determined.

Water Content of the Hydrogel

The hydrogel was dried at 110° C. for 6 hours to thoroughly remove the water contained therein. The water content of the hydrogel was determined from the gel weight $W_0$ and weight $W_1$, in gram, prior to and after drying, respectively, by the following formula;

Water content of hydrogel=$[(W_0-W_1)/W_0]\times 100$

Endothermic Peak Temperature of Polyvinyl Alcohol

The hydrogel was heated at 150° C. for 10 minutes to thoroughly remove the water contained therein. The resulting polyvinyl alcohol was ground to determine the endothermic peak temperature in nitrogen atmosphere under the condition of a temperature elevation rate of 10° C./min by differential scanning thermal analysis (with an analyzer TYPE DSC-30 manufactured by Metzler, Co. Ltd.).

Resistance to Hot Water of the Hydrogel

The hydrogel was cut into test pieces of a size 20 mm×20 mm. The test pieces were processed in hot water at 130° C. for one hour. The resistance to hot water of the test pieces was evaluated and ranked as good (○), when the test pieces remained transparent after the hot-water processing and the same size as before the hot-water processing was kept along with the same gel shape; or the resistance was ranked as poor (x) when the test pieces lost transparency after the hot-water processing or the pieces were at different sizes or of different shapes from those before the hot-water processing or the pieces were solubilized by the hot-water processing.

The hydrogel was cut into test pieces of a size 20 mm×20 mm, and the test pieces were subjected to a hot water process in isotonic sodium chloride solution at 121° C. for 20 minutes. The resistance to hot water of the test pieces was evaluated and ranked as good (○) when the test pieces remained transparent after the hot-water processing and before the hot-water processing was kept along with the same gel shape; or the resistance was ranked as poor (x) when the test pieces lost transparency after the hot-water processing or the pieces were at different sizes or of different shapes from those before the hot-water processing or the pieces were solubilized by the hot-water processing.

Handleability of the Hydrogel

The hydrogel was cut into test pieces of a size 20 mm×20 mm, and the test pieces were picked up with a dental faucet. The handleability of the gel was evaluated and ranked as good (○) when the test pieces could be picked up with no break; or the handleability was ranked as poor (x) when the test pieces were broken and could not be picked up.

Flexibility of the Hydrogel

The hydrogel was cut into test pieces of a size 20 mm×20 mm, and one end thereof was bent until in contact with the other end. The flexibility of the test pieces was evaluated and ranked as good (○) when the test pieces could be bent with almost no force and the ends could be made to contact one another without a break or no crack; or the flexibility was ranked as poor (x) when the test pieces could never be in contact to the other end or break or crack occurred in the gel during bending.

Transparency of the Hydrogel

The hydrogel was ground into a size of about 1 to 2 mm, and the ground gel was fully packed in a isotonic sodium chloride solution-filled photocell for absorbance determination with a 10-mm optical path length. Then, the transmittance at a wave length of 700 nm was measured with a spectrophotometer Type DU-65 manufactured by Beckman, Co. Ltd.. The ratio (%) of the transmittance was calculated with reference to the transmittance of isotonic sodium chloride solution, which was designated 100%.

Water Absorption Ratio

The hydrogel was dried at room temperature for 24 hours under reduced pressure to completely remove the water contained therein and the dry weight $W_2$ in grams was determined. The dried product was immersed in isotonic sodium chloride solution at 37° C. for 24 hours to absorb isotonic sodium chloride solution up to the saturation state. The weight $W_3$ (g) then was measured. The water absorption ratio was determined as the ratio of the weight $W_3$ after the absorption of isotonic sodium chloride solution to the dry weight $W_2$ (g).

Amount of Solubilized Matter from the Hydrogel

A sample of the hydrogel (1 g) was placed in isotonic sodium chloride solution (10 ml), and the gel was heated to 37° C. for 24 hours. The total organic carbon (TOC) contained in the isotonic sodium chloride solution was then analyzed by a total organic carbon meter Type TOC-5000 manufactured by Shimadzu, Co. Ltd. The resulting TOC was defined as the amount of solubilized matter from the hydrogel.

Example 2

By the same procedures as in Example 1, a partially saponified polyvinyl alcohol containing the same structural unit (I) as in Example 1 was produced.

The polyvinyl alcohol (10 g) containing the structural unit (I) was charged, together with distilled water (90 g), into an autoclave for processing at 130° C. for 3 hours. Bromoacetic acid (0.56 g) and sodium hydroxide (0.34 g) were added to the resulting mixture for reaction under boiling and agitation for 6 hours. Consequently, a particulate polymer was recovered and washed in water prior to drying. The dried polymer was dissolved in 95 g of a mixture of water/propanol=3/7 (w/w), and the resulting solution was poured over a glass plate, which was then immersed overnight in water at 25° C. for gelation. The resulting hydrogel was excellent in terms of flexibility and transparency.

By the same manner as in Example 1, determination and assessment were made of the hydrogel and the polyvinyl alcohol composing the hydrogel, concerning the molar fraction of the structural unit (II), the average chain length ($L_{est}$) of the structural unit (I), water content, endothermic peak temperature, resistance to hot water, handleability, flexibility, transparency, water absorption ratio, and the amount of solubilized matters. The results are shown in the following Table 1.

Example 3

By the same procedures as in Example 1, a partially saponified polyvinyl alcohol (namely, a partially saponified polyvinyl pivalate) with the molar fraction of the structural unit (I) of 0.37, a syndiotacticity of 61% and a viscosity average polymerization degree of 1650, was produced.

The partially saponified polyvinyl alcohol (10 g), was dissolved in dimethylsulfoxide (190 g). The same procedures as in Example 1 were followed, except for the addition of succinic anhydride (0.85 g) and pyridine (0.66 g), to produce a hydrogel of a sheet type. The resulting hydrogel sheet had excellent flexibility and transparency.

By the same manner as in Example 1, the molar fraction of the structural unit (II), the average chain length ($L_{est}$) of the structural unit (I), water content, endothermic peak temperature, resistance to hot water, handleability, flexibility, transparency, water absorption ratio, and the amount of solubilized matters of the hydrogel and the polyvinyl alcohol composing the hydrogel, were determined. The results are shown in the following Table 1.

Comparative Example 1

Using a partially saponified polyvinyl alcohol containing the vinyl acetate unit at a molar fraction of 0.12 and having a syndiotacticity of 53% and a viscosity average polymerization degree of 1700, instead of the partially saponified polyvinyl alcohol containing the structural unit (I) recovered in Example 1, the same hydrogel preparation step reaction as in Example 1 was effected. The resulting water-containing product had such an extremely low strength that the product could not retain the sheet shape. Therefore, the product was useless as a hydrogel.

By the same manner as in Example 1, the average chain length ($L_{est}$) of the structural unit (vinyl acetate unit), water content, endothermic peak temperature, resistance to hot water, handleability, flexibility, transparency, water absorption ratio, and the amount of solubilized matter of the water-containing product and the polyvinyl alcohol composing the water-containing product, were determined. The results are shown in the following Table 2.

Comparative Example 2

A partially saponified polyvinyl alcohol containing the vinyl acetate unit at a molar fraction of 0.015 and having a syndiotacticity of 53% and a viscosity average polymerization degree of 1700 was used, instead of the partially saponified polyvinyl alcohol containing the structural unit (I) recovered in Example 1. The polyvinyl alcohol (5 g) was mixed and dissolved into an aqueous solution containing 10% glycerine under heating, and the whole resulting aqueous solution was poured over a polystyrene plate, followed by freezing at −20° C. and thawing at room temperature in repetition three times, to recover a hydrogel in sheet form, comprising the partially saponified polyvinyl alcohol. The resulting hydrogel was white and opaque, and was solubilized under boiling in water.

By the same manner as in Example 1, the average chain length ($L_{est}$) of the structural unit (vinyl acetate unit), water content, endothermic peak temperature, resistance to hot water, handleability, flexibility, transparency, water absorption ratio, and the amount of solubilized matter of the hydrogel and the partially saponified polyvinyl alcohol composing the hydrogel, were determined. The results are shown in the following Table 2.

Comparative Example 3

By the same procedures as in Example 1, a partially saponified polyvinyl alcohol (namely, a partially saponified polyvinyl pivalate) with the molar fraction of the structural unit (I) of 0.001, a syndiotacticity of 61% and a viscosity average polymerization degree, of 1650, was produced.

The partially saponified polyvinyl alcohol (10 g), was dissolved in dimethylsulfoxide (190 g). The same procedures as in Example 1, were followed except for the addition of succinic anhydride (0.85 g) and pyridine (0.66 g), to produce a hydrogel of a sheet type. The resulting hydrogel sheet was transparent, but had an extremely low strength. Thus, the gel could not retain the sheet form.

By the same manner as in Example 1, the average chain length ($L_{est}$) of the structural unit (vinyl pivalate unit), water content, endothermic peak temperature, resistance to hot water, handleability, flexibility, transparency, water absorption ratio, and the amount of solubilized matters of the hydrogel and the polyvinyl alcohol composing the hydrogel, were determined. The results are shown in the following Table 2.

Comparative Example 4

The same partially saponified polyvinyl alcohol (namely, the partially saponified polyvinyl acetate) (10 g) as in Comparative Example 2 was charged into a mixture of dimethylsulfoxide (50 ml) and water (50 ml), prior to heating at 90° C. for 2 hours under stirring for dissolution, and the resulting solution was subsequently cooled down to 60° C. Twenty milliliters of an aqueous 25% solution of a copolymer of methyl vinyl ether/maleic anhydride (manufactured by Aldrich, Co. Ltd.; molecular weight of 20,000) were added to the resulting cooled solution, which was then stirred at 60° C. for another 30 minutes. The entire resulting solution was poured over a polystyrene tray (240-mm length×240-mm width), followed by cooling down to room temperature. The resulting solution was left to stand at −20° C. for 14 hours, to recover a semi-transparent gel. After washing the gel in water, the gel was left to stand in isotonic sodium chloride solution for about 24 hours, to prepare a hydrogel of a sheet type.

By the same manner as in Example 1, the average chain length ($L_{est}$) of the structural unit (vinyl acetate unit), water content, endothermic peak temperature, resistance to hot water, handleability, flexibility, transparency, water absorption ratio, and the amount of solubilized matter of the hydrogel and the partially saponified polyvinyl alcohol composing the hydrogel, were determined. The results are shown in the following Table 2.

TABLE 1

|  | Example 1 | Example 2 | Example 3 |
| --- | --- | --- | --- |
| [Polyvinyl alcohol] | | | |
| Structural unit (I) | | | |
| $R^1$ | $CH_3$ | $CH_3$ | $CH_3$ |
| $R^2$ | $CH_3$ | $CH_3$ | $CH_3$ |
| $R^3$ | $CH_3$ | $CH_3$ | $CH_3$ |
| Molar fraction | 0.19 | 0.19 | 0.37 |
| Structural unit (II) | | | |
| Chemical formula | IIa-1 | IIa-4 | IIa-1 |
|  | (m = 2) | (n = 1) | (m = 2) |
| Molar fraction | 0.012 | 0.012 | 0.018 |
| $L_{est}$ | 4.8 | 4.8 | 9.9 |
| Viscosity average polymerization degree | 1650 | 1650 | 1650 |
| Syndiotacticity (%) | 61 | 61 | 61 |
| Endothermic peak temperature (°C.) | 171 | 173 | —[3] |
| [Hydrogel] | | | |
| Water absorption ratio | 9.2 | 9.5 | 3.0 |
| Water content (%) | 89.1 | 89.5 | 66.7 |
| Resistance of hot water (a)[1] | ○ | ○ | ○ |
| Resistance of hot water (b)[2] | ○ | ○ | ○ |
| Handleability | ○ | ○ | ○ |
| Flexibility | ○ | ○ | ○ |
| Transmittance (%) | 79 | 74 | 48 |
| Solubilized matters (ppm) | 0 | 0 | 0.2 |

[1]Resistance to hot water at a heating process in hot water at 130° C. for one hour.
[2]Resistance to hot water at a heating process in isotonic sodium chloride solution at 121° C. for 20 minutes.
[3]No distinct endothermic peak temperature observed.

TABLE 2

|  | Comparative example 1 | Comparative example 2 | Comparative example 3 | Comparative example 4 |
| --- | --- | --- | --- | --- |
| [Polyvinyl alcohol] | | | | |
| Structural unit (I) | | | | |
| $R^1$ | H | H | $CH_3$ | H |
| $R^2$ | H | H | $CH_3$ | H |
| $R^3$ | H | H | $CH_3$ | H |
| Molar fraction | 0.12 | 0.015 | 0.001 | 0.015 |
| Structural unit (II) | | | | |
| Chemical formula | IIa-1 | — | IIa-1 | — |
|  | (m = 2) | — | (m = 2) | — |
| Molar fraction | 0.013 | — | 0.020 | — |
| $L_{est}$ | 2.3 | 2.7 | —[4] | — |
| Viscosity average polymerization degree | 1700 | 1700 | 1650 | 1700 |
| Syndiotacticity (%) | 53 | 53 | 61 | 53 |
| Endothermic peak temperature (°C.) | —[3] | 220 | —[3] | 220 |
| [Hydrogel] | | | | |
| Water absorption ratio | —[3] | 15.6 | —[3] | 32.9 |
| Water content (%) | —[3] | 93.6 | —[3] | 97.0 |
| Resistance to hot water (a)[1] | —[3] | x | —[3] | x |
| Resistance to hot water (b)[2] | —[3] | x | —[3] | x |

TABLE 2-continued

|  | Comparative example 1 | Comparative example 2 | Comparative example 3 | Comparative example 4 |
|---|---|---|---|---|
| Handleability | —[3] | ○ | —[3] | x |
| Flexibility | —[3] | ○ | —[3] | ○ |
| Transmittance (%) | —[3] | 0.5 | —[3] | 29 |
| Solubilized matters (ppm) | —[3] | 389.1 | —[3] | 51.5 |

[1] Resistance to hot water at a heating process in hot water at 130° C. for one hour.
[2] Resistance to hot water at a heating process in isotonic sodium chloride solution at 121° C. for 20 minutes.
[3] No hydrogel with shape retention formed. No determination or evaluation made.
[4] No determination because of larger influence of the structural unit (II).

The results in Tables 1 and 2 indicate that the hydrogels of Examples 1 to 3, which were prepared from the polyvinyl alcohol of the present invention, showed excellent transparency, flexibility, resistance to hot water, and handleability, involving no or extremely less solubilized matter. These gels thus provide greater safety in wound dressing.

The results of Tables 1 and 2 furthermore indicate that Comparative Examples 1 to 4, never satisfying both of the requirements (i) and (ii), did not form any hydrogel or formed only poor hydrogels with poor resistance to hot water and poor transparency, involving more solubilized matter and lower strength.

Reference Example 1

The structural unit (I)-containing partially saponified polyvinyl alcohol recovered in Example 1, corresponds to the polymer described in U.S. Pat. No. 5,187,226 issued to the present applicant. For reference, therefore, a 5% solution of the partially saponified polyvinyl alcohol in dimethylsulfoxide was poured on a glass plate and immersed then in water, to prepare a hydrogel.

By the aforementioned methods, the physico-chemical properties of the resulting hydrogel recovered were examined. The gel was excellent like the gels of Examples 1 to 3, concerning resistance to hot water, handleability, transparency and solubilized matter. When the hydrogel was bent so as to evaluate the flexibility, the gel could be bent with no occurrence of break or crack, but spring-like repulsive forces developed during gel bending, which indicates that the gel had lower flexibility than the hydrogels of Examples 1 to 3.

Example 4

A partially saponified polyvinyl alcohol (10 g) containing the structural unit (I) produced in the same manner as in Example 1, wherein the molar fraction of the structural unit (I), syndiotacticity and viscosity average polymerization degree were 0.19, 61% and 1650, respectively, was dissolved in dimethylsulfoxide (190 g), followed by addition of succinic anhydride (0.41 g) and pyridine (0.32 g) for reaction at 110° C. for one hour. The resulting solution (about 200 g) was poured over a polystyrene tray (240-mm length× 240-mm width), which was then immersed in water at 25° C. overnight for gelation. The gel was washed sufficiently in water to recover a hydrogel of a sheet type, comprising a polyvinyl alcohol modified with a carboxyl group represented by the formula (II) wherein X is a group represented by the formula —CO—CH$_2$CH2—COOH.

By the same manner as in Example 1, the content of the carboxyl group in the hydrogel was determined at 12.2 μmol. From the results, the molar fraction of the carboxyl group-containing structural unit in the polyvinyl alcohol composing the hydrogel, was calculated to be 0.012, by the same manner as in Example 1.

By the same manner as in Example 1, the endothermic peak temperature of the hydrogel and the average chain length ($L_{est}$) of the structural unit (I) were measured to be 171° C. and 4.8, respectively. By the same procedure as in Example 1, the water content of the hydrogel was 97.2% by weight. Even after one-hour treatment in water at 130° C., the gel retained the transparent gel form.

The sheet-type hydrogel (21.1 g) was immersed in an aqueous 50% dimethylformamide solution, followed by addition of N-hydroxysuccinimide (23 mg; manufactured by Peptide Research Institute) and water soluble carboximide (200 mg; manufactured by Peptide Research Institute), for shaking overnight at room temperature. Then, taurine (25 mg; manufactured by WAKO Chemical Industry, Co. Ltd.) and triethylamine (16 g 1; manufactured by Nakarai Tesque, Co. Ltd.) were added to the resulting mixture for overnight shaking at room temperature. Subsequently, the resulting product was washed thoroughly in water, prior to substitution with isotonic sodium chloride solution, to prepare a sulfo group-containing hydrogel of a sheet type, having excellent transparency and flexibility [hydrogel comprising the polyvinyl alcohol wherein the structural unit (II) was a structural unit represented by the aforementioned chemical formula (IIb-5)].

The water absorption ratio and water content of the sulfo group-containing hydrogel were determined to be 11.0 and 91% by weight, respectively.

Sampling and sufficiently washing a part of the sulfo group-containing hydrogel in water, prior to acetone substitution, the resulting product was dried under reduced pressure. After calcining the resulting product in an oxygen atmosphere and making the product absorb pure water, the product was quantitatively analyzed by an ion chromato-analyzer (Type IC 500 S, manufactured by Yokogawa Electric, Co. Ltd.). The sulfur content thereof was 0.12% by weight, and the molar fraction of the structural unit (II) [a structural unit represented by the chemical formula (IIb-5)] was 0.0023 on the basis of the sulfur content. The IR spectrum of a potassium bromide tablet containing the sulfo group-containing hydrogel showed characteristic peaks of 1732 cm$^{-1}$ corresponding to ester an group and 1635 cm$^{-1}$ corresponding to an amide group under observation.

The resistance to hot water, handleability, flexibility, transparency, water absorption ratio, and the amount of solubilized matter of the sulfo group-containing hydrogel were determined in the same manner as in Example 1. The results are shown in the following Table 3.

Example 5

A partially saponified polyvinyl alcohol (6 g) containing the structural unit (I) was produced in the same manner as in Example 1, wherein the molar fraction of the structural unit (I), syndiotacticity and viscosity average polymerization degree were 0.19, 61% and 1650, respectively, and dissolved in dimethylsulfoxide (200 g), followed by addition of succinic anhydride (0.55 g) and pyridine (0.43 g) for reaction under agitation and heating at 70° C. for about 3 hours. The resulting solution (about 200 g) was poured over a polystyrene tray (225-mm length×225-mm width), which was then immersed in water at 25° C. overnight for gelation. After washing the resulting gel in water, a hydrogel of a sheet type was formed, comprising a polyvinyl alcohol modified with a carboxyl group represented by the formula (II) wherein X is a group represented by the formula —CO—$CH_2CH_2$—COOH.

By the same manner as in Example 1, the content of the carboxyl group in the hydrogel was determined. From the results, the molar fraction of the carboxyl group-containing structural unit in the polyvinyl alcohol composing the hydrogel was calculated to be 0.011.

The endothermic peak temperature of the hydrogel and the average chain length ($L_{est}$) of the structural unit (1) were measured to be 173° C. and 4.8, respectively. The water content of the hydrogel was 89.5% by weight. Even after one hour treatment in water at 130° C., the gel retained the transparent gel form.

The sheet-type hydrogel (21.1 g) was sampled for reaction with taurine in the same manner as in Example 4. The resulting product was washed then thoroughly in water, prior to substitution with isotonic sodium chloride solution, to prepare a sulfo group-containing hydrogel of a sheet type, having excellent transparency and flexibility [hydrogel comprising the polyvinyl alcohol wherein the structural unit (II) was a structural unit represented by the aforementioned chemical formula (IIb-5)].

The water absorption ratio and water content of the sulfo group-containing hydrogel were determined to be 9.1 and 89% by weight, respectively.

A part of the sulfo group-containing hydrogel was sampled for quantitative analysis by an ion chromatoanalyzer in the same manner as in Example 4. The sulfur content thereof was 0.12% by weight, and the molar fraction of the structural unit (II) [a structural unit represented by the chemical formula (IIb-5)] was 0.0019 on the basis of the sulfur content. The IR spectrum of a potassium bromide tablet containing the sulfo group containing hydrogel, showed characteristic peaks of 1732 $cm^{-1}$ corresponding to an ester group and 1635 $cm^{-1}$ corresponding to an amide group under observation.

The resistance to hot water, handleability, flexibility, transparency, water absorption ratio, and the amount of solubilized matters of the sulfo group-containing hydrogel were determined in the same manner as in Example 1. The results are shown in the following Table 3.

Example 6

A partially saponified polyvinyl alcohol (5 g) containing the structural unit (I) was produced in the same manner as in Example 1, wherein the molar fraction of the structural unit (I), syndiotacticity and viscosity average polymerization degree were 0.19, 61% and 1650, respectively, and was dissolved in dimethylsulfoxide (150 g) under heating and agitation at about 80° C. The resulting solution (about 150 g) was poured over a polystyrene tray (225-mm length×225-mm width), which was then immersed in water at 25° C. overnight for gelation. After washing the gel in water, a hydrogel of a sheet type was recovered.

The average chain length ($L_{est}$) of the structural unit (I) of the hydrogel was determined at 4.8.

To the sheet-type hydrogel (15 g) were added epichlorohydrin (10 ml; manufactured by WAKO Chemical Co. Ltd.) and an aqueous 3N sodium hydroxide solution (20 ml), for reaction under heating and agitation at 40° C. for 4 hours. Subsequently, the product was washed in pure water three times, followed by addition of an aqueous 25% ammonia solution (20 ml) for reaction under heating and stirring at 40° C. for 3 hours. The resulting product was thoroughly washed in water, prior to substitution with isotonic sodium chloride solution, to prepare a sheet-type hydrogel containing an amino group and having good transparency and fine flexibility [a polyvinyl alcohol hydrogel wherein the structural unit (II) was a structural unit represented by the chemical formula (IIc-6)].

The water absorption ratio and water content of the amino group-containing hydrogel were determined to be 3.3 and 69% by weight, respectively.

A part of the amino group-containing hydrogel was sampled for elemental analysis of the nitrogen content thereof. The nitrogen content was 0.28% by weight, and the molar fraction of the structural unit (II) [a structural unit represented by the chemical formula (IIb-6)] was 0.0038 on the basis of the nitrogen content. The IR spectrum of a potassium bromide tablet containing the amino group-containing hydrogel, showed characteristic peaks of 1730 $cm^{-1}$ corresponding to an ester group and 1647 $cm^{-1}$ corresponding to an amino group under observation.

The resistance to hot water, handleability, flexibility, transparency, water absorption ratio, and the amount of solubilized matters of the amino group-containing hydrogel were determined in the same manner as in Example 1. The results are shown in the following Table 3.

Example 7

A partially saponified polyvinyl alcohol (5 g) containing the structural unit (I) was produced in the same manner as in Example 1, wherein the molar fraction of the structural unit (I), syndiotacticity and viscosity average polymerization degree were 0.19, 61% and 1650, respectively, and was then dissolved in dimethylsulfoxide (150 g) under heating at about 80° C. and stirring. The resulting solution (about 150 g) was poured over a polystyrene tray (225-mm length×225-mm width), which was then immersed in water at 25° C. overnight for gelation. After washing the resulting gel in water, a hydrogel of a sheet type was recovered.

The average chain length ($L_{est}$) of the structural unit (I) of the hydrogel was determined at 4.8.

The water in the sheet-type hydrogel (15 g) was substituted with dimethylformamide, followed by addition of phosphorus pentaoxide (0.5 g; manufactured by WAKO Chemical, Co. Ltd.) and methane sulfonic acid (0.2 g), for reaction at room temperature for 4 hours. The resulting product was thoroughly washed in pure water, prior to substitution with isotonic sodium chloride solution, to prepare a sheet-type hydrogel containing a phosphonooxy group and having good transparency and fine flexibility [a polyvinyl alcohol hydrogel wherein the structural unit (II) was a structural unit represented by the chemical formula (IId-1)].

The water absorption ratio and water content of the phosphonooxy group-containing hydrogel were determined to be 6.7 and 85% by weight, respectively.

A part of the phosphonooxy group-containing hydrogel was sampled for analysis of the phosphorus content by an ion chromato-analyzer in the same manner as in Example 4. The phosphorus content thereof was 0.43% by weight, and the molar fraction of the structural unit (II) [a structural unit represented by the chemical formula (IId-1)] was 0.0084 on the basis of the phosphorus content.

The resistance to hot water, handleability, flexibility, transparency, water absorption ratio, and the amount of solubilized matter of the phosphonooxy group-containing hydrogel were determined. in the same manner as in Example 1. The results are shown in the following Table 3.

Comparative Example 5

A partially saponified polyvinyl alcohol containing the vinyl acetate unit at a molar fraction of 0.12 and having a syndiotacticity of 53% and a viscosity average polymerization degree of 1700, was used, instead of the partially saponified polyvinyl alcohol containing the structural unit (I) recovered in Example 5. The polyvinyl alcohol reacted with taurine in the same manner as in Example 4, but the resulting water-containing product had such an extremely low strength that the product could not retain the sheet form. Thus, the product was useless as a hydrogel.

The average chain length ($L_{est}$) of the structural unit (vinyl acetate unit), water content, endothermic peak temperature, resistance to hot water, handleability, flexibility, transparency, water absorption ratio, and the amount of solubilized matter of the hydrogel and the polyvinyl alcohol composing the water-containing product, were determined. The results are shown in the following Table 4.

Comparative Example 6

By the same procedures as in Example 1, a partially saponified polyvinyl alcohol with a molar fraction of the structural unit (I) of 0.001, a syndiotacticity of 61% and a viscosity average polymerization degree of 1650 (namely, a partially saponified polyvinyl pivalate), was produced.

The partially saponified polyvinyl alcohol containing the structural unit (I), was prepared as a 5% dimethylsulfoxide solution. After the resulting solution was reacted with taurine in the same manner as in Example 4, the solution was poured over a polystyrene tray and then immersed in water for gelation. The resulting gel was transparent, but had an extremely low strength. Thus, the gel could not retain the sheet form.

Determination of the average chain length ($L_{est}$) of the structural unit (vinyl pivalate unit) was attempted, but no significant value could be obtained because of larger influence of the sulfo group-containing structural unit structural unit (II).

TABLE 3

|  | Example 4 | Example 5 | Example 6 | Example 7 |
|---|---|---|---|---|
| [Polyvinyl alcohol] Structural unit (I) |  |  |  |  |
| $R^1$ | $CH_3$ | $CH_3$ | $CH_3$ | $CH_3$ |
| $R^2$ | $CH_3$ | $CH_3$ | $CH_3$ | $CH_3$ |
| $R^3$ | $CH_3$ | $CH_3$ | $CH_3$ | $CH_3$ |
| Molar fraction | 0.19 | 0.19 | 0.19 | 0.19 |
| Structural unit (II) |  |  |  |  |
| Chemical formula | IIb-5 (r =2, s = 2) | IIb-5 (r = 2, s = 2) | IIc-6 | IId-1 |
| Molar fraction | 0.0023 | 0.0019 | 0.0038 | 0.0084 |

TABLE 3-continued

|  | Example 4 | Example 5 | Example 6 | Example 7 |
|---|---|---|---|---|
| $L_{est}$ | 4.8 | 4.8 | 4.8 | 4.8 |
| Viscosity average polymerization degree | 1650 | 1650 | 1650 | 1650 |
| Syndiotacticity (%) | 61 | 61 | 61 | 61 |
| [Hydrogel] |  |  |  |  |
| Water absorption ratio | 11.1 | 9.1 | 3.3 | 6.7 |
| Water content (%) | 91 | 89 | 69 | 85 |
| Resistance to hot water (a)[1] | ○ | ○ | ○ | ○ |
| Resistance to hot water (b)[2] | ○ | ○ | ○ | ○ |
| Handleability | ○ | ○ | ○ | ○ |
| Flexibility | ○ | ○ | ○ | ○ |
| Transmittance (%) | 79 | 74 | 48 | 64 |
| Solubilized matters (ppm) | 0 | 0 | 0.2 | 0 |

[1] Resistance to hot water at a heating process in hot water at 130° C. for one hour.
[2] Resistance to hot water at a heating process in isotonic sodium chloride solution at 121° C. for 20 minutes.

TABLE 4

|  | Comparative example 5 | Comparative example 6 |
|---|---|---|
| [Polyvinyl alcohol] Structural unit (I) |  |  |
| $R^1$ | H | $CH_3$ |
| $R^2$ | H | $CH_3$ |
| $R^3$ | H | $CH_3$ |
| Molar fraction | 0.12 | 0.001 |
| Structural unit (II) |  |  |
| Chemical formula | IIb-5 (r = 2, s = 2) | IIb-5 (r = 2, s = 2) |
| Molar fraction | 0.013 | 0.020 |
| $L_{est}$ | 2.3 | —[4] |
| Viscosity average polymerization degree | 1700 | 1650 |
| Syndiotacticity (%) | —[3] | —[3] |
| [Hydrogel] |  |  |
| Water absorptian ratio | —[3] | —[3] |
| Water content (%) | —[3] | —[3] |
| Resistance to hot water (a)[1] | —[3] | —[3] |
| Resistance to hot water (b)[2] | —[3] | —[3] |
| Handleability | —[3] | —[3] |
| Flexibility | —[3] | —[3] |
| Transmittance (%) | —[3] | —[3] |
| Solubilized matters (ppm) | —[3] | —[3] |

[1] Resistance to hot water at a heating process in hot water at 130° C. for one hour.
[2] Resistance to hot water at a heating process in isotonic sodium chloride solution at 121° C. for 20 minutes.
[3] No hydrogel with shape retention formed. No determination or evaluation made.
[4] No determination because of larger influence of the structural unit (II).

The results in Tables 3 and 4 indicate that the hydrogels of Examples 4 to 7, which were prepared from the polyvinyl alcohol of the present invention, showed excellent transparency, flexibility, resistance to hot water, and handleability, involving no or extremely less solubilized matters, at greater safety.

The results of Tables 3 and 4 furthermore indicate that Comparative Examples 5 to 6, never satisfied both of the requirements (i) and (ii) and, did not form any hydrogel or formed only practically useless hydrogels with extremely low strength.

Test Example 1

Porcine Model of Full-Thickness Defective Wounds

Eight full-thickness defective wounds of a size of 20 mm×20 mm were prepared on the dorsal part of a pig (of age 4 weeks). The sheet-type hydrogel recovered in Example 1, was cut into pieces of a size of 20 mm×20 mm and then steam sterilized at 121° C. in isotonic sodium chloride solution for 20 minutes. The pieces were attached as a wound dressing material onto two of the full-thickness defective wounds for 6 days. The wound dressing material was so transparent that the healing process of the wounds could be observed very well through the material from outside.

The sheet-type hydrogel comprising the partially saponified polyvinyl alcohol, recovered in Comparative Example 2, was cut into pieces of a size of 20 mm×20 mm, which were then attached as a wound dressing material onto two of the full-thickness defective wounds for 6 days. The wound dressing material was so opaque that the healing process of the wounds could never be observed through the material from outside during the testing period.

The sheet-type hydrogel comprising the partially saponified polyvinyl alcohol and the copolymer of methyl vinyl ether/maleic anhydride, recovered in Comparative Example 4, was cut into pieces of a size of 20 mm×20 mm, and the pieces were attached as a wound dressing material onto two of the full-thickness defective wounds for 6 days. The wound dressing material was so semi-transparent that the healing process of the wounds could be observed only slightly through the material from outside during the testing period.

A commercially available polyurethane film wound dressing material (BIOCLUSIVE; manufactured by Johnson & Johnson Medical Inc.) as a control was cut into pieces of a size of 40 mm×40 mm and the pieces were attached as a wound dressing material onto two of the full-thickness defective wounds for 6 days.

On day 6 of the aforementioned tests tissue specimens were individually sampled from the wounds, followed by routine hematoxylin-eosin staining to examine the state of granulation in growth in the tissue specimens. Simultaneously, the infiltration of inflammatory cells was evaluated to observe the intensity of the reaction to foreign bodies. Comparing with the above commercial control, assessments were made of the wound dressing materials. When granulation in growth was promoted, involving very good healing of wounds, the material was ranked as "good"; when granulation in growth was poor, involving poor healing of wounds, the material was ranked as "bad"; when the intensity of reaction to foreign bodies was weak, the material was ranked as "good"; when the intensity of the reaction was strong, the material was ranked as "bad". The results are shown in the following Table 5.

TABLE 5

| hydrogel wound dressing material | Granulation in growth | Reaction to foreign bodies |
| --- | --- | --- |
| Material of Example 1 | Good | Good (weak) |
| Material of Comparative Example 2 | Good | Bad (strong) |
| Material of Comparative Example 4 | Bad | Bad (strong) |

The results in Table 5 above indicate that the wound dressing material of Example 1 of the present invention, comprising the polyvinyl alcohol containing the structural units (I) and (II) at the molar fractions satisfying the requirements (i) and (ii), can rapidly promote the healing of wounds, involving granulation in growth with no occurrence of reaction to foreign bodies in wounds. In contrast, the wound dressing material of Comparative Example 2 can promote granulation in growth well but causes strong reaction to foreign bodies at poor safety and the wound dressing material of Comparative Example 4 slowly promotes granulation in growth, never involving smooth healing of wounds and additionally, the material causes strong reaction to foreign bodies, so that the material is not sufficiently safe.

Test Example 2

Porcine Model of Full-Thickness Defective Wounds

Eight full-thickness defective wounds of a size of 20 mm×20 mm were prepared on the dorsal part of a pig (of age 4 weeks). The sheet-type hydrogel recovered in Example 1, and the hydrogel recovered in Reference Example 1, were steam sterilized in isotonic sodium chloride solution at 121° C. for 20 minutes, and wound dressing materials of a size 20 mm×20 mm from the resulting sterilized gels. Four sheets of each of the materials were attached on the wounds. Then, every three days, the materials were exchanged for new materials of the same type. During the testing period for 18 days, the state of the wounds was observed through the transparent wound dressing materials. On day 18, the areas of the wounds attached with the two types of the wound dressing materials were individually measured to be both 10 mm$^2$ on average of the four wounds (the areas of the wounds were initially 400 mm$^2$ at the test). Thus, the remaining ratio of the wound areas was as small as 2.5%, which indicates smooth healing of the wounds. Additionally, no symptom of keloid or hypertrophic scar was observed on any of the wounds. The wounds demonstrated normal healing.

The wound sites on day 18 were excised along with the circumferential skin and supporting muscle layer, and the excised tissues were fixed in neutral formalin and embedded in paraffin, to prepare sections of 5 μm. The sections were stained with hematoxylin-eosin, to quantitatively observe the presence and level of the residue of the wound dressing material fragments (foreign bodies) and foreign body giant cells. In accordance with Chakravarthy, D., et. al., *Evaluation of three new hydrocolloid dressings; Retention of dressing integrity and biodegradability of absorbent components attenuate inflammation. J. Biomed. Mater. Res.,* 28, 1165–1173 (1994), the outcome was ranked and scored individually as 0 (no), 1 (slight), 2 (normal) and 3 (notable). Consequently, the four wounds covered with the wound dressing material from the hydrogel of Example 1, were ranked as score 0 as to residue (foreign body) of the wound dressing material fragments and the presence of foreign body giant cells; the four wounds covered with the wound dressing material from the hydrogel of Reference Example 1 were ranked as follows; three of them were ranked as score 1 and one ranked as score 2, as to residue (foreign body) of the wound dressing material fragments and the presence of foreign body giant cells.

Test Example 3

Porcine Model of Partial-Thickness Defective Wounds

Two Young male pigs (of an average body weight of 15 kg), domestically bred, were used for testing. On the porcine dorsal part were made two partial-thickness defective wounds of a 22 mm square size by means of an electric dermatome. The wound dressing material recovered in Example 1, was attached to individual wounds. On day 5, the wounds on the two pigs were all occluded, with no scar or keloid observed. On the same day, the wounds were excised along with the circumferential skin and supporting muscle layer. The excised tissues were fixed in neutral formalin and embedded in paraffin, to prepare sections of 5 gm. The sections were stained with hematoxylin-eosin, to quantitatively observe the presence and level of any residue of wound dressing material fragments (foreign bodies) and foreign body giant cells. In the same manner as in Test Example 2, the outcome was scored. Consequently, the residue (foreign body) of wound dressing material fragments and the presence of foreign body giant cells were all scored 0 on all the wounds of the two pigs.

This application is based on Japanese Patent Applications 350488/1995 and 185466/1996, filed with the Japanese Patent Office on Dec. 22, 1995 and Jun. 26, 1996, respectively, the entire contents of which are hereby incorporated by reference.

Obviously, additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A wound dressing material comprising a gel produced from a polyvinyl alcohol comprising (i) one or more structural units represented by the following formula (I):

wherein $R^1$ is hydrogen atom or a mono-valent hydrocarbon; and $R^2$ and $R^3$ are, independently, a mono-valent hydrocarbon group or $R^2$ and $R^3$ together form a ring along with the carbon atom to which $R^2$ and $R^3$ are bonded; or $R^1$, $R^2$ and $R^3$ together form a ring along with the carbon atoms to which $R^1$, $R^2$ and $R^3$ are bonded, wherein the structural units of formula (I) are present at a molar fraction of 0.05 to 0.50; and (ii) at least one structural unit represented by the following formula (II):

wherein X is a group represented by the formula —CO—Y, -Y or —COCOOH, wherein Y represents a hydrocarbon group modified with at least one polar group selected from the group consisting of carboxyl, sulfo, amino and phosphonooxy groups; or a hydrocarbon group modified with a group having at least one polar group selected from the group consisting of carboxyl, sulfo, amino and phosphonooxy groups; or X forms a phosphonooxy group together with the oxygen atom to which X is bonded, wherein the structural units of formula (II) are present at a molar fraction of 0.0001 to 0.50.

2. The wound dressing material as claimed in claim 1, further comprising one or more pharmaceutically acceptable additives selected from the group consisting of softening agents, stabilizers, divalent metal ions having pharmacological activity, anti-bacterial agents, blood circulation improving agents, growth factors, enzyme inhibitors and anti-inflammatory agents.

* * * * *